(12) United States Patent
Borkon

(10) Patent No.: US 8,097,014 B2
(45) Date of Patent: Jan. 17, 2012

(54) VARIABLE RIGIDITY VAGINAL DILATOR AND USE THEREOF

(75) Inventor: William D. Borkon, Shorewood, MN (US)

(73) Assignee: William D. Borkon, Minnetonka, MN (US)

( * ) Notice: Subject to any disclaimer, the term of this patent is extended or adjusted under 35 U.S.C. 154(b) by 608 days.

(21) Appl. No.: 12/286,418

(22) Filed: Sep. 30, 2008

(65) Prior Publication Data

US 2010/0082057 A1 Apr. 1, 2010

(51) Int. Cl.
*A61M 29/00* (2006.01)

(52) U.S. Cl. ........................................................ 606/193

(58) Field of Classification Search ............... 606/193, 606/191, 192; 601/45; 128/834, 845
See application file for complete search history.

(56) References Cited

U.S. PATENT DOCUMENTS

| | | |
|---|---|---|
| 1,735,519 A | 11/1929 | Vance |
| 2,499,045 A | 2/1950 | Walker et al. |
| 3,799,170 A | 3/1974 | Walsh et al. |
| 3,882,852 A | 5/1975 | Sinnreich |
| 3,900,033 A | 8/1975 | Leininger et al. |
| 3,954,102 A | 5/1976 | Buuck |
| 4,137,922 A | 2/1979 | Leininger et al. |
| 4,228,801 A | 10/1980 | Magnasco et al. |
| 4,237,893 A | 12/1980 | Michaels |
| 4,267,829 A | 5/1981 | Burton et al. |
| 4,383,525 A | 5/1983 | Scott et al. |
| 4,407,278 A | 10/1983 | Burton et al. |
| 4,590,927 A | 5/1986 | Porter et al. |
| 4,664,114 A | 5/1987 | Ghodsian |
| 5,010,882 A | 4/1991 | Polyak et al. |
| 5,065,772 A | 11/1991 | Cox |
| 5,141,509 A | 8/1992 | Burton et al. |
| 5,254,092 A | 10/1993 | Polyak |
| 5,263,981 A | 11/1993 | Polyak et al. |
| 5,499,994 A | 3/1996 | Tihon et al. |
| 5,681,340 A | 10/1997 | Veronikis |
| 5,704,895 A | 1/1998 | Scott et al. |
| 5,947,992 A | 9/1999 | Zadini et al. |
| 6,443,887 B1 | 9/2002 | Derus et al. |
| 6,533,719 B2 | 3/2003 | Kuyava |
| 6,558,315 B1 | 5/2003 | Kuyava |
| 6,723,042 B2 | 4/2004 | Almli et al. |

(Continued)

OTHER PUBLICATIONS

Mediator's CerDilator/MD-12 http://www.hcegroup.com/vpage.jsp?vpage_id=2256.

(Continued)

*Primary Examiner* — Gary Jackson
*Assistant Examiner* — Lindsey Bachman

(57) ABSTRACT

Relatively pain free vaginal dilation is obtained by inserting into the vaginal canal a variable rigidity vaginal dilator having an inflatable balloon, in a manner that avoids insertion into the urethra. Air is introduced into the balloon. When the patient has gained confidence in the pain free use of the dilator, the balloon is deflated to remove the air and water is introduced into the balloon to expand it so that it contacts the vaginal canal and exerts a pressure thereon. This contact is maintained for a period of up to about 15 minutes. The pressure and/or contact time is stepwise sequentially increased to a maximum of about 12 atmospheres and a contact time of up to about 45 minutes, in accordance with a regimen and instructions established by the patient's healthcare provider and tailored to the patient's specific needs. A preferred embodiment of the dilator and a kit employing same, useful in the method of the invention, are disclosed.

1 Claim, 4 Drawing Sheets

U.S. PATENT DOCUMENTS

| | | |
|---|---|---|
| 6,730,017 B2 | 5/2004 | Henkel et al. |
| 6,808,489 B2 | 10/2004 | George et al. |
| 6,808,490 B1 | 10/2004 | Ling et al. |
| 6,929,599 B2 | 8/2005 | Westrum |
| 6,935,847 B2 | 8/2005 | Kuava et al. |
| 7,066,876 B2 | 6/2006 | Westrum |
| 7,066,877 B2 | 6/2006 | Kuyava et al. |
| 7,066,878 B2 | 6/2006 | Eid |
| 2001/0007945 A1* | 7/2001 | Piraka .......... 606/193 |
| 2003/0087734 A1* | 5/2003 | Kring et al. ......... 482/112 |
| 2003/0114878 A1* | 6/2003 | Diederich et al. ......... 606/192 |
| 2004/0116955 A1* | 6/2004 | Foltz et al. ......... 606/193 |
| 2004/0127931 A1 | 7/2004 | Kincaid et al. |
| 2006/0200187 A1 | 9/2006 | Gude |
| 2006/0271092 A1 | 11/2006 | Reed et al. |
| 2008/0215031 A1* | 9/2008 | Belfort et al. ......... 604/500 |

OTHER PUBLICATIONS

Bard Eagle Inflation Device REF 325110,C.R.Bard,Inc. Covington, GA.

Bard UroForce Ref 887604, C.R.Bard, Inc. Covington, GA.

UroMax Ultra, Boston Scientific Corporation, Natick, MA.

Medilator http://otek.org.il/eng/graduate_projects.php?p_id=25 (Print version) pp. 1-3 / Medilator presentation at Medica 2003.

\* cited by examiner

VARIABLE RIGIDITY VAGINAL DILATOR AND USE THEREOF

BACKGROUND OF THE INVENTION

As the medical community begins to understand and treat Female Sexual Dysfunction (FSD) numerous treatments are emerging. Dyspareunia is one form of FSD. Dyspareunia is caused by many anatomic and psychological problems. Some of the anatomic problems include pelvic surgery, vaginal stenosis and atrophy associated with aging or hormonal changes, radiation, transgender surgery, congenital abnormalities, and numerous other vaginal diseases. Psychological issues such as rape, abuse, anxiety, pelvic pain syndromes, and even lack of basic sexual education, can all have a devastating affect on women wanting to engage in vaginal intercourse, and are even more common than the anatomic causes of pain.

All of these causes, and others, are amenable to treatment by the vaginal dilation program of the present invention, such process being carefully designed for the individual patient by a therapist and/or physician.

Vaginal dilators are known in the prior art. For example, U.S. Pat. No. 5,681,340 discloses a vaginal dilator the length of which is adjustable. The device of the '340 patent is typical of what has been employed in the prior art for vaginal dilation. It is a rigid non-expandable dilator. The advantage of such dilators is that they are relatively inexpensive. However, they do not work with all patients.

U.S. Pat. No. 5,947,992 discloses an inflatable menstrual cup for preventing blood leakage. An inflatable member having an inflatable reservoir for collection of menstrual blood or organic fluids is inserted into the vaginal canal and inflated by pneumatic means so that it sealingly engages the vaginal wall. The pneumatic means can be provided by chemical reaction of components contained within the inflatable member.

U.S. Pat. Nos. 3,900,033 and 4,137,922 disclose an inflatable dilator for the cervical canal. The dilator comprises an envelope member having an enlarged bulbous portion on one end and a shield at the opposite end. The envelope member is inflatable with suitable gases such as carbon dioxide, or liquids such as saline, distilled water and the like. As is seen from the drawings, the dilator of these patents comprises an inserter tube provided with ports through which gas or liquid can be introduced through the tube into a relatively non-expansible envelope for the purpose of dilating the cervix.

U.S. Patent Application 20060200187 discloses a vaginal obturator device for preparing the vaginal area for delivery of a fetus during childbirth. The device comprises an elongated hollow shaft insertable in a vaginal opening during childbirth.

U.S. Pat. No. 4,228,801 discloses a dilator comprised of an at least partially hollow body made of an elastically deformable material defining a cavity that is hydro-pneumatically connected to a source of pressurized fluid by means of a substantially rigid duct. A valve is provided to control the hydro-pneumatic communication between the cavity and the source of pressurized fluid. When the dilator is positioned in situ, pressurized fluid is introduced through the duct and expands the body.

U.S. Pat. No. 1,735,519 discloses a nasal dilator designed so that principal dilation occurs at the distal end (i.e. the head or nose) of the instrument. To accomplish this the thickness of the wall is graduated, with the thinnest portion being disposed near the head.

Cervical dilators have also been reported in the literature. For example, MeDilator's "CerDilator"/"MD-12" uses a disposable inflatable catheter to dilate the cervix.

None of the above discussed prior art dilators is suitable for patient use of a dilator in the home in a method of treatment that allows for substantially pain-free vaginal dilation.

SUMMARY OF THE INVENTION

The present invention provides a variable rigidity vaginal dilator and a method of utilizing same in a treatment program carefully designed for the individual patient by a therapist and/or physician.

The inflatable variable rigidity vaginal dilator of the present invention facilitates vaginal dilation and allows the patient complete control of the dilating process.

The inflatable variable rigidity vaginal dilator of the present invention is accompanied by instructions for its use that, with the help of the patient's health-care professional, is customized to the patient's needs.

Although several dilating devices exist, even inflatable devices, none is specifically designed to allow the patient to control every aspect of the process, in a safe, private, carefully graduated dilation program that is carried out in the patient's home. The device and method of the present invention is designed to allow a woman to comfortably carry out vaginal dilation in her own home and without assistance.

BRIEF DESCRIPTION OF THE DRAWINGS

The device of the present invention and method of using such device in accordance with the treatment program of the present invention will now be explained with reference to the accompanying drawings in which.

DETAILED DESCRIPTION

Figure 1:
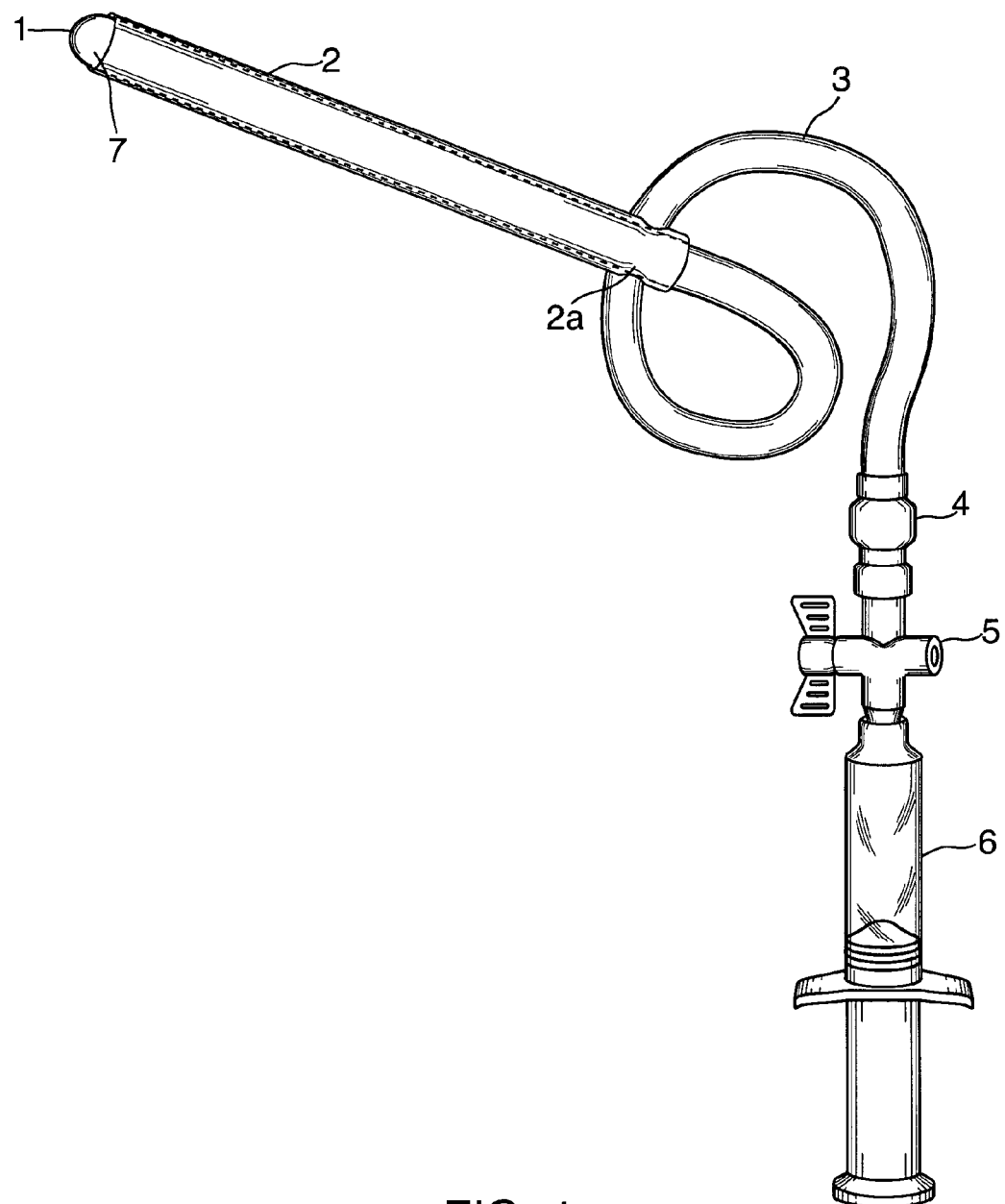
FIG. 1 is a perspective view of a preferred device employable in the method of the instant invention showing the sheath overlying the collapsed expandable balloon.
Figure 2:
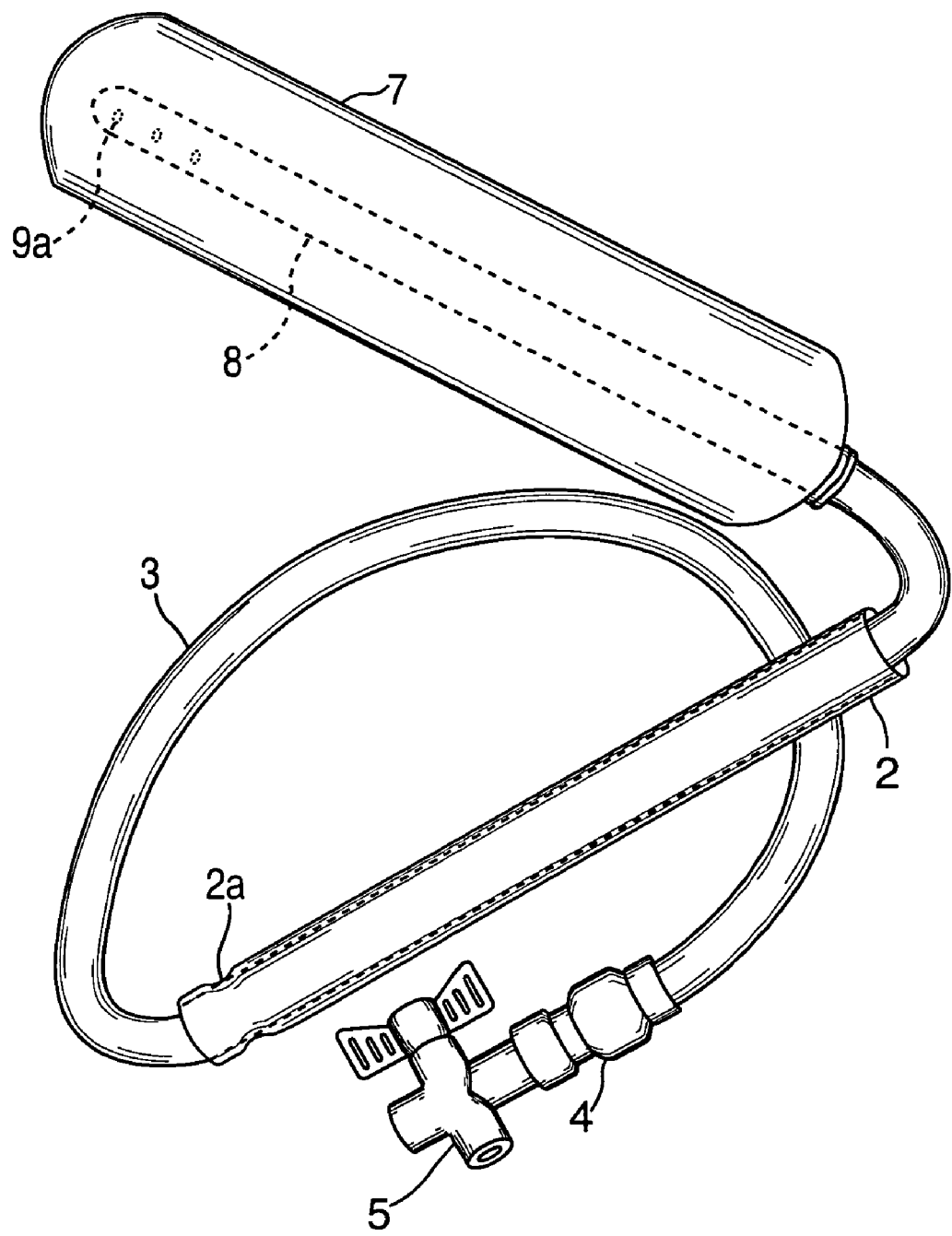
FIG. 2 is a perspective view of the device of FIG. 1 showing the sheath moved back to expose the balloon, the balloon inflated and the stopcock closed.

As shown in FIGS. 1 through 4, the variable rigidity vaginal dilating device of the present invention is comprised of a catheter 8 having a plurality of ports 9a, an inflatable member or balloon 7, a tubular member 3, a valve and stopcock 5, a syringe 6 or pump 10, and, optionally, an inline pressure gauge 11.

At least a portion of catheter 8 is disposed within inflatable balloon 7. Preferably, substantially all of catheter 8 is disposed within inflatable balloon 7. More preferably, all of catheter 8 is disposed within inflatable balloon 7.

One end of catheter 8 extends within balloon 7. The other end of catheter 8 is fixed to balloon 7 and to one end of tubular member 3, in a fluid (i.e. water and air) tight manner. The other end of tubular member 3 is fixed to a valve or stopcock 5, in a fluid (i.e. water and air) tight manner.

An air and liquid tight seal between tubular member 3 and stopcock 5 can suitably be obtained by means of a friction fitting 4 or a like air and liquid tight seal well known to those skilled in the art.

Stopcock 5 communicates with a Luer Lock piston syringe 6 or with a pump 10 and an optional inline pressure gauge 11. Syringe 6 is adapted to be filled with air or water, depending on the stage of treatment that the patient is in, and will vary in size dependent upon the size of balloon 7.

When balloon 7 is inflated to the desired diameter and pressure, stopcock 5 is closed so that the syringe can be removed and the inflated balloon 7 left in the vagina for the desired period of time.

A tubular sheath 2 overlies and substantially encases balloon 7 when balloon 7 is not inflated and is in its collapsed state. Tubular sheath 2 is open at its proximal and distal ends. When balloon 7 is positioned within sheath 2, the distal end of sheath 2 is adjacent the distal end of balloon 7 and the proximate end of sheath 2 is adjacent the end of tubular member 3.

Sheath 2 is provided with a finger gripping surface, such as indent 2a, which facilitates grasping sheath 2 so it can be moved backwards toward tubular member 3 to a position at which balloon 7 is fully exposed and sheath 2 overlies and encases a portion of tubular member 3.

Sheath 2 becomes more important after several uses of the device, because with repeated use balloon 7 tends to lose its shape.

Preferably, each device is accompanied by a diagram of the vagina 12, with particular emphasis on the location of the urethra 13. Since the only potential harm of use of the device would be accidental dilation of the urethra, this complication is described in detail and technical advice is provided on how to avoid insertion into the urethra 13. Preferably, the device is also supplied with lubricant and cleaning instructions.

Balloon 7 is substantially fluid (gas and liquid) impermeable. Preferably, it is fluid (gas & liquid) impermeable.

Balloon 7 is in fluid communication with a fluid reservoir. Pneumatic means external to balloon 7 and positioned outside of the vaginal canal is employed to pump fluid from the fluid reservoir into balloon 7.

Figure 3:
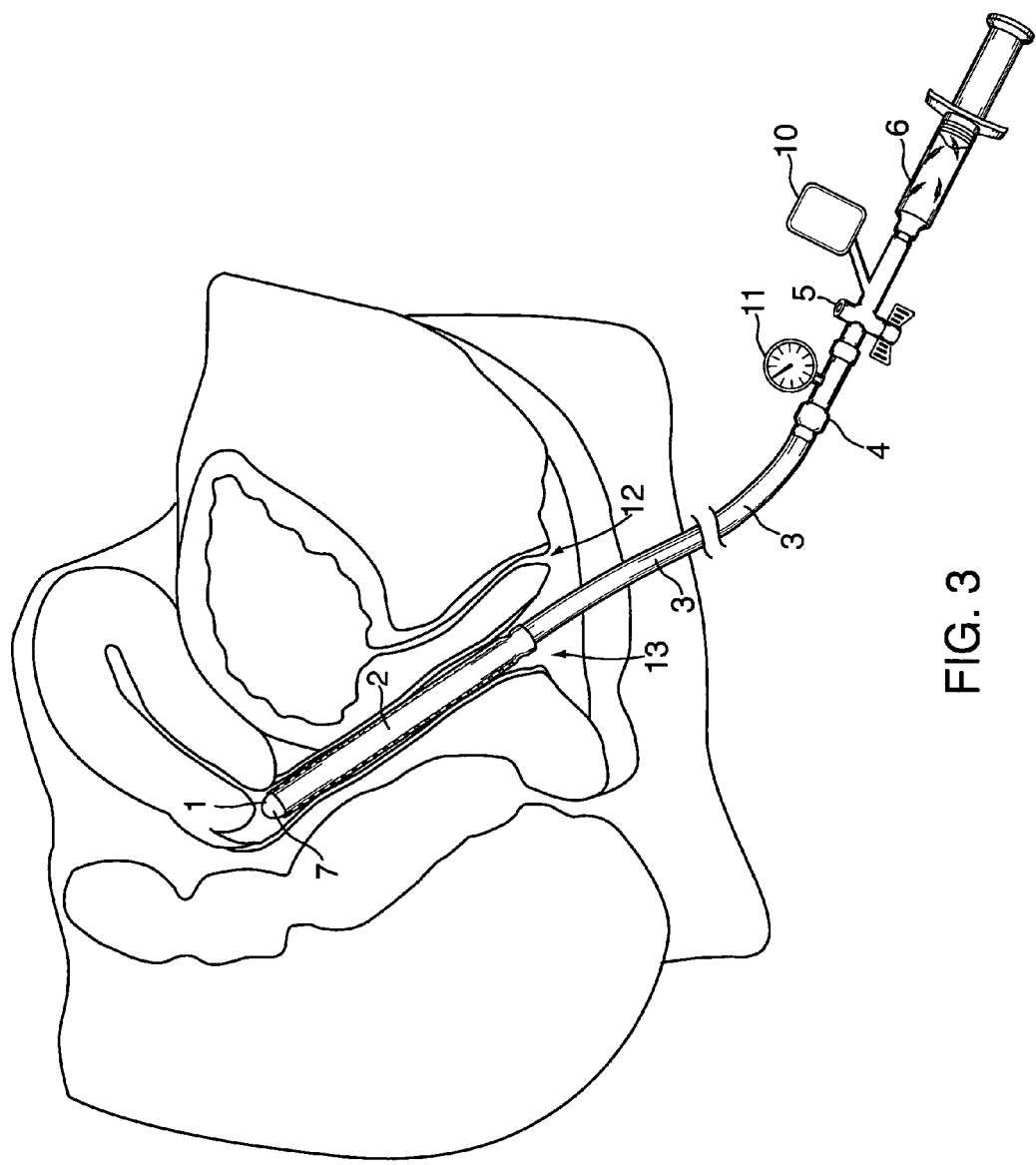
FIG. 3 shows the device of FIG. 1 positioned in the vagina.
Figure 4:
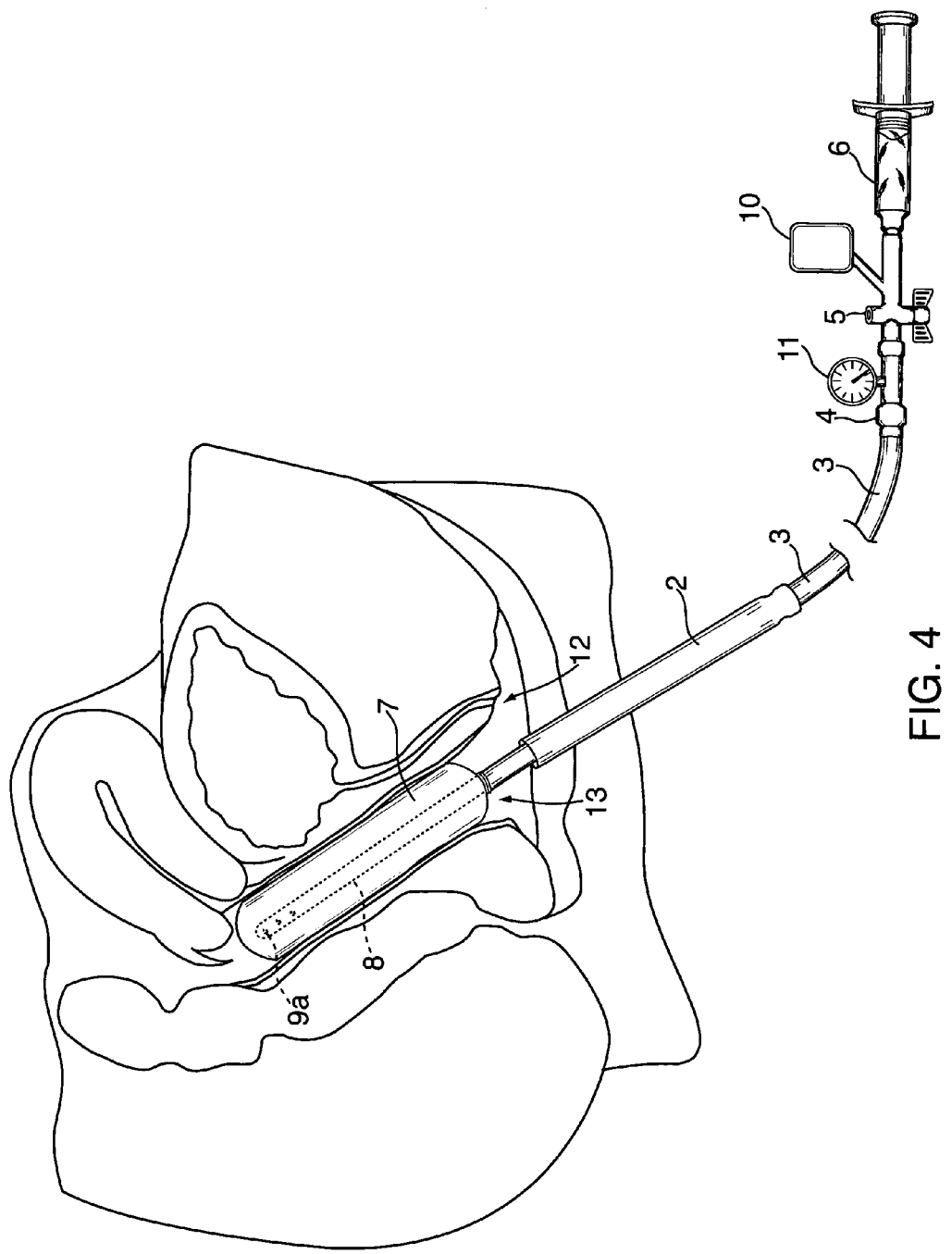
FIG. 4 shows the device of FIG. 2 positioned in the vagina.

When inserted into the vaginal canal, as shown in FIG. 3, and inflated by the pneumatic means the balloon 7 expands to contact the walls of the vaginal canal, as shown in FIG. 4. The amount of pressure exerted against the walls of the vaginal canal depends upon the amount of fluid pumped into balloon 7.

The amount of fluid pumped in should be sufficient to produce a predetermined pressure against the vaginal walls contacted. The amount of fluid pumped in and the time that the resultant inflated balloon 7 is permitted to remain in contact with the vaginal canal walls is selected such that a predetermined desired degree of dilation of the vaginal canal obtained. This degree of dilation should be selected so that the vaginal tissues are gently stretched, preferably with minimal or no pain.

Balloon 7 is fabricated of a strong expansible material to allow for inflation and deflation. The material employed should be substantially impermeable to fluids, such as air and water. Preferably it should be impermeable to air and water.

Balloon 7 is preferably shaped to compliment the vagina. Preferably, the wall thickness of balloon 7 is substantially uniform over the length of balloon 7.

Balloon 7 can be made of natural rubber latex, silicone, polyurethane, hydrophilic coated polymers, or like materials. Silastic® (a silicone elastomer available from Dow Corning) and Nydex® nylon can be used. Other suitable expansible materials that can be employed in the manufacture of balloon 7 are well known to those skilled in the art.

Hydrophyllic coatings, special polymers, polyurethane, silicone and latex are relatively inexpensive, strong, elastic and possess good barrier protection.

Optionally, a pressure gauge 11 is positioned outside the vaginal canal and in fluid communication with the interior of balloon 7, so that the pressure within the inflated balloon 7 can be determined. Stopcock 5 is also positioned outside the vaginal canal and in fluid communication with the interior of balloon 7. When stopcock 5 is closed, the fluid pressure in the inflated balloon 7 is maintained. When stopcock 5 is opened, fluid will exit the inflated balloon 7 and fluid pressure within the inflated balloon 7 will be reduced, facilitating removal from the vagina.

In accordance with the method of the present invention, a woman will begin dilation at whatever diameter she is comfortable with down to an 8 French diameter. The length of the inflatable member (also referred to herein as an inflatable "balloon") is also variable. Whatever the balloon length, the depth of vaginal penetration is patient controlled.

Initial dilations are done with air filling the balloon. This results in a soft malleable balloon that really does not dilate the vaginal wall. It merely functions to prepare the patient's vagina for dilation in an a traumatic manner. Because the inflatable balloon is soft at the beginning of the treatment, it gives the woman confidence in the safety and comfort of the dilation process.

At the beginning of the treatment, the air filled balloon will generally have a rigidity of up to about ½ atmosphere. As the patient gains confidence in the use of the dilator in accordance with the method of the invention she will increase rigidity up to about 1 atmosphere. After getting used to this level of rigidity she will increase the rigidity up to about 2 atmospheres pressure.

After the patient has gained confidence in the procedure through use of the air filled balloon, she will reduce the balloon diameter and restart the dilating process by filling the balloon with liquid (preferably, water) instead of air.

When completely full, the water filled balloon is rock hard. In the early stage of treatment with the water filled balloon, rigidity of the water filled balloon will be up to about 8 atmospheres pressure. As the treatment regimen progresses rigidity of the water filled balloon will be increased to up to about 10 atmospheres pressure. In cases of severe scarring the rigidity of the water filled balloon called for by the treatment regimen may be increased up to a maximum of about 12 atmospheres pressure.

The balloon's diameter and length are controlled by the patient. During the phase of the treatment regimen in which the air filled balloon is employed and during the phase of the treatment regimen in which the water filled balloon is employed, the patient will gradually increase both diameter and length of the balloon as well as contact or holding time (i.e. the time the expanded balloon is left in place in the vagina to exert pressure against the contacted vaginal canal wall), in accordance with the treatment regimen established for the patient by her health care provider, until the desired result is obtained.

The balloon's diameter, length and rigidity and the amount of holding time the expanded balloon is left in the vaginal canal should be such as to produce minimal pain, preferably no pain. Naturally this will vary from patient to patient.

In general, holding time will initially be from about 5 to about 15 minutes. As the patient gains confidence and as the treatment regimen progresses and she increases balloon rigidity (and, consequently, increases pressure exerted against the vaginal wall) she will increase holding time from about 20 to about 30 minutes. As the treatment regimen progresses further she will increase holding time to from about 30 to about 45 minutes. Application of high pressure for longer periods is not desirable. If at any point in the treatment regimen the patient is very uncomfortable she can shorten the hold time.

Every patient has a different pain threshold. The dilator and treatment regimen of the present invention permits each patient to adjust pressure and/or hold time so as to minimize (preferably, eliminate) pain. The end result is a reduction in pelvic pain, allowing more comfortable vaginal intercourse.

The present invention also includes within its ambit, a vaginal dilation kit that includes a plurality of variable rigidity vaginal dilators, in accordance with the present invention; a vaginal lubricant for facilitating introduction of the dilator into the vaginal canal; instructions for introducing the dilator into the vaginal canal in a manner that avoids insertion into the patient's urethra; and written indicia setting forth a regimen prepared by the patient's healthcare provider and tailored to the patient's specific needs. The regimen specifies the procedure for using the dilator including, pressure within the balloon, time the inflated balloon is to remain in the vaginal canal (dwell time) at such pressure, the procedure for deflating the balloon; and like information for successive courses of treatment during which pressure and dwell time are periodically increased.

What is claimed is:

1. A method for treating dyspareunia in a patient suffering from dyspareunia comprising:
   a) providing a variable rigidity vaginal dilator comprising:
      i) a catheter having a first end and a second end, the catheter having a plurality of ports adjacent the first end;
      ii) an inflatable balloon open at one end but being otherwise closed, the balloon being made of a material that is impermeable to air and water;
      iii) a syringe or pump;
   b) inserting into the vaginal canal of said patient said inflatable balloon of said variable rigidity vaginal dilator;
   c) initially introducing air into the balloon and then deflating the balloon to remove the air, this process is performed at least once;
   d) introducing water into the balloon to expand it so that it contacts the vaginal canal and exerts a pressure thereon of about 8 atmospheres and maintaining such contact for a period of about 15 minutes;
   e) stepwise sequentially increasing pressure up to about 12 atmospheres and/or stepwise sequentially increasing contact time up to about 45 minutes, the pressure and duration of contact adjusted as to secure, in a relatively pain-free manner, vaginal dilation sufficient to ameliorate the dyspareunia.

* * * * *